US006986179B2

(12) United States Patent
Varadharajulu et al.

(10) Patent No.: US 6,986,179 B2
(45) Date of Patent: Jan. 17, 2006

(54) GROUTED TILTING PATIENT POSITIONING TABLE FOR VASCULAR APPLICATIONS

(75) Inventors: Muthuvelan Varadharajulu, Chennai (IN); Rajagopal Narayanasamy, Bangalore (IN); Baskar Somasundaram, Bangalore (IN); Shaji Alakkat, Bangalore (IN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 15 days.

(21) Appl. No.: 10/065,866

(22) Filed: Nov. 26, 2002

(65) Prior Publication Data

US 2004/0098804 A1    May 27, 2004

(51) Int. Cl.
*A61G 13/04* (2006.01)
*A61G 13/06* (2006.01)
*A61B 6/04* (2006.01)

(52) U.S. Cl. .................... 5/611; 5/610; 5/601; 378/209
(58) Field of Classification Search .................... 5/611, 5/11, 600, 601, 610, 608; 378/209
See application file for complete search history.

(56) References Cited

U.S. PATENT DOCUMENTS

| 1,118,851 | A |   | 11/1914 | Turner |
|-----------|---|---|---------|--------|
| 1,444,042 | A |   | 2/1923  | Schwalbach |
| 3,588,500 | A | * | 6/1971  | Koerner ......................... 5/601 |
| 3,944,204 | A | * | 3/1976  | Cesar ............................. 5/601 |
| 4,013,019 | A | * | 3/1977  | Horsey .......................... 108/5 |
| 4,071,222 | A | * | 1/1978  | Wright ....................... 254/8 C |
| 4,435,862 | A | * | 3/1984  | King et al. ..................... 5/611 |
| 4,452,439 | A | * | 6/1984  | Hogan ........................... 5/601 |
| 4,475,072 | A | * | 10/1984 | Schwehr et al. ............ 318/602 |
| 4,484,571 | A | * | 11/1984 | Velazquez ...................... 5/601 |
| 4,541,108 | A |   | 9/1985  | Grady et al. ................. 378/196 |
| 4,597,119 | A |   | 7/1986  | Padgett |
| 4,715,591 | A |   | 12/1987 | Dragmen, Sr. ................. 5/601 |
| 4,731,889 | A | * | 3/1988  | Ishikawa ....................... 5/607 |
| 4,751,754 | A | * | 6/1988  | Bailey et al. .................. 5/611 |
| 4,761,000 | A |   | 8/1988  | Fisher et al. .................. 5/608 |
| 4,769,584 | A |   | 9/1988  | Irigoyen et al. ............ 318/648 |
| 4,771,785 | A | * | 9/1988  | Duer .......................... 600/415 |
| 4,841,585 | A | * | 6/1989  | Masuzawa ..................... 5/610 |
| 4,908,844 | A | * | 3/1990  | Hasegawa ................... 378/209 |

(Continued)

FOREIGN PATENT DOCUMENTS

DE    EPO 268 555 B1    9/1991

(Continued)

*Primary Examiner*—Robert G. Santos
(74) *Attorney, Agent, or Firm*—McAndrews, Held & Malloy, Ltd.; Peter J. Vogel; Michael A. Dellapenna

(57) ABSTRACT

Certain embodiments include a system and method for positioning a patient with a patient positioning system. The system includes a patient positioning surface for supporting a patient. The system also includes a lift subsystem for adjusting elevation of the patient positioning surface, a longitudinal subsystem for moving the patient positioning surface in a longitudinal direction, a lateral subsystem for moving the patient positioning surface in a lateral direction, a tilt subsystem for tilting the patient positioning surface, and a rotation subsystem for rotating the patient positioning surface. The system further includes a control subsystem for controlling operation of the patient positioning system and a base affixed to a floor for securing the patient positioning system. The control subsystem may perform iso-center tracking to maintain a region of interest of the patient in an image area during tilt. The control subsystem may also avoid collision with the ground and/or predetermined objects.

34 Claims, 10 Drawing Sheets

U.S. PATENT DOCUMENTS

| | | | |
|---|---|---|---|
| 4,912,754 A * | 3/1990 | Van Steenburg | 378/209 |
| 4,944,500 A * | 7/1990 | Mueller et al. | 5/600 |
| 4,953,243 A * | 9/1990 | Birkmann | 5/600 |
| 5,013,018 A * | 5/1991 | Sicek et al. | 5/601 |
| 5,014,292 A * | 5/1991 | Siczek et al. | 378/196 |
| 5,048,071 A * | 9/1991 | Van Steenburg | 378/209 |
| 5,156,166 A | 10/1992 | Sebring | |
| 5,205,004 A | 4/1993 | Hayes et al. | |
| 5,210,893 A * | 5/1993 | Uosaki et al. | 5/601 |
| 5,237,600 A * | 8/1993 | Kamata | 378/177 |
| 5,272,776 A * | 12/1993 | Kitamura | 5/601 |
| 5,386,453 A * | 1/1995 | Harrawood et al. | 378/196 |
| 5,398,356 A * | 3/1995 | Pfleger | 5/608 |
| 5,572,569 A * | 11/1996 | Benoit et al. | 378/209 |
| 5,590,429 A * | 1/1997 | Boomgaarden et al. | 5/600 |
| 5,596,779 A * | 1/1997 | Meek | 5/600 |
| 5,659,909 A * | 8/1997 | Pfeuffer et al. | 5/600 |
| 6,038,718 A | 3/2000 | Pennington et al. | |
| 6,094,760 A * | 8/2000 | Nonaka et al. | 5/601 |
| 6,192,585 B1 | 2/2001 | Buchanan et al. | |
| 6,240,582 B1 * | 6/2001 | Reinke | 5/601 |
| 6,249,695 B1 * | 6/2001 | Damadian | 600/427 |
| 6,269,499 B1 | 8/2001 | Amir | |
| 6,334,708 B1 * | 1/2002 | Kosugi | 378/197 |
| 6,353,949 B1 | 3/2002 | Falbo | |
| 6,470,519 B1 | 10/2002 | Pattee et al. | |
| 6,541,973 B1 * | 4/2003 | Danby et al. | 324/318 |
| 6,566,833 B2 | 5/2003 | Bartlett | |
| 6,615,428 B1 * | 9/2003 | Pattee | 5/601 |
| 6,615,429 B2 * | 9/2003 | Weil et al. | 5/601 |
| 6,651,279 B1 * | 11/2003 | Muthuvelan | 5/600 |
| 6,769,145 B1 | 8/2004 | Pfeuffer et al. | |
| 6,769,806 B2 * | 8/2004 | Moyers | 378/204 |
| 6,857,147 B2 * | 2/2005 | Somasundaram | 5/601 |
| 2002/0029419 A1 * | 3/2002 | Weil et al. | 5/601 |
| 2002/0120986 A1 * | 9/2002 | Erbel et al. | 5/601 |
| 2003/0053599 A1 * | 3/2003 | Meyer et al. | 378/196 |
| 2003/0145383 A1 | 8/2003 | Schwaegerle | 5/610 |
| 2004/0028188 A1 * | 2/2004 | Amann et al. | 378/209 |
| 2004/0098804 A1 * | 5/2004 | Varadharajulu et al. | 5/611 |
| 2004/0139545 A1 | 7/2004 | Reinke et al. | |
| 2004/0172756 A1 * | 9/2004 | Somasundaram | 5/600 |
| 2004/0172757 A1 * | 9/2004 | Somasundaram | 5/601 |
| 2004/0172758 A1 * | 9/2004 | Alakkat | 5/610 |
| 2005/0114996 A1 * | 6/2005 | Somasundaram | 5/601 |
| 2005/0129181 A1 * | 6/2005 | Shinoda | 378/209 |

FOREIGN PATENT DOCUMENTS

EP            119910 A * 9/1984

* cited by examiner

Collapsed Condition

Expanded Condition

Forward tilt (head down)

Reverse tilt (head up)

ROTATION: +90°
Rotated to RH side when viewed from rear of table

ROTATION: -90°
Rotated to LH side when viewed from rear of table

Up-Down & Rotation (Patient Loading)

Longitudinal Travel (Scanning)

Longitudinal Tilt (Vascular Tilt)

Longitudinal Axis

Head Up tilt (Positive)

Head Down tilt (Negative)

Highest Postion

Lowest Postion

Fwd. Tilt Position

Reverse Tilt Position

HEAD - DOWN TILT

HEAD - UP TILT

ISO-CENTER TRACKING

GROUTED TILTING PATIENT POSITIONING TABLE FOR VASCULAR APPLICATIONS

BACKGROUND OF INVENTION

The present invention generally relates to a patient positioning platform. In particular, the present invention relates to a patient positioning platform with particular use in vascular applications.

Patient positioner platforms allow a medical practitioner, such as a doctor, nurse or technician, to position a patient during a medical procedure, such as XR, CT, EBT, nuclear, and PET procedures. Patient positioner platforms, such as tables or other supports, allow a patient to be elevated, moved in lateral & longitudinal directions, rotated and/or tilted during a procedure. Patient positioning platforms improve a medical practitioner's ability to examine and/or perform a medical procedure on a patient.

There is a need for an improved patient positioning platform that may be used in angiography, neurology, and cardiac procedures. Current patient positioner platforms may introduce limitations in obtaining images of blood flow in arteries, heart, lungs, or brain, for example. Thus, a patient positioning system that improves stability and reliable positioning for blood flow imaging in angiography, neurology, cardiac and other such procedures would be highly desirable.

Additionally, there is a need for an improved patient positioning platform that may be used for emerging vascular procedures, such as emergent situations, venous access, and $CO_2$ studies. Emergent situations include emergency, life-threatening or serious situations, such as falling artery pressure or a blood vessel rupture, that prompt immediate medical attention. Proper and easy positioning of a patient may help a medical practitioner provide treatment to correct the emergent situation. Venous access relates to insertion of a catheter into a patient for introduction or retrieval of fluids in a patient's veins. Proper and easy positioning of a patient may aid insertion of the catheter as well as introduction or extraction of materials through the catheter. $CO_2$ studies involve injecting carbon dioxide as a contrast agent in patient veins. While $CO_2$ is excreted on the first pass of the blood through the lungs, it is desirable to limit the possibility of contamination or toxicity in certain areas of the body, such as the brain. Proper and reliable positioning of a patient may help reduce the chance of $CO_2$ contamination during $CO_2$ studies of the patient.

Currently, patient positioner platforms possess limitations in properly positioning a patient for vascular applications, such as emergent situations, venous access, and $CO_2$ studies. Additionally, many current patient positioner platforms lack flexibility to accommodate emergent situations, venous access, and $CO_2$ studies of a patient. Therefore, a patient positioning system that provides reliable and easy positioning of a patient with flexibility to accommodate a variety of vascular applications, such as emergent situations, venous access, and $CO_2$ studies, would be highly desirable.

Thus, a need exists for a patient positioning system that provides a reliable, flexible and complete solution for vascular and other medical applications.

SUMMARY OF INVENTION

Certain embodiments include a system and method for positioning a patient with a patient positioning system. The system includes a patient positioning surface for supporting a patient. The system also includes a lift subsystem for adjusting elevation of the patient positioning surface, a longitudinal subsystem for moving the patient positioning surface in a longitudinal direction, a lateral subsystem for moving the patient positioning surface in a lateral direction, a tilt subsystem for tilting the patient positioning surface, and a rotation subsystem for rotating the patient positioning surface. The system further includes a control subsystem for controlling operation of the patient positioning system. The control subsystem may also avoid collision with the ground and/or predetermined objects.

In a certain embodiment, the control subsystem performs iso-center tracking to maintain a region of interest of the patient in an image area during tilt. The lift subsystem adjusts elevation of the patient positioning surface using a two-stage synchronized telescopic lift system. The longitudinal subsystem moves the patient positioning surface in a longitudinal direction using a two-stage synchronized telescopic longitudinal system. The longitudinal and lateral subsystems allow manual or motorized movement of the patient positioning surface in lateral direction and/or longitudinal direction.

The system may also include a base affixed to a floor for securing the patient positioning system. The system may also include patient restraints for securing the patient to the patient positioning surface. The system may also include a power-on brake for braking when a voltage is supplied to the power-on brake and a power-off brake for braking when a voltage is removed from the power-off brake. The system may further include at least one encoder for determining the position of the patient positioning surface. The encoder may allow the patient positioning surface to return to a recorded position.

The method includes vertically positioning a patient positioning surface to a desired height to allow a patient to be loaded onto the patient positioning surface, rotating the patient positioning surface to a position to allow a patient to be loaded onto the patient positioning surface, and loading a patient on the patient positioning surface. The method further includes positioning the patient for a medical procedure by rotating, lifting, lateral motion, longitudinal motion, and/or longitudinal tilting of the patient positioning surface. The method also includes maintaining a region of interest of the patient during movement of the patient positioning surface.

The method may also include unloading the patient from the patient positioning surface. The method may also include returning the patient positioning surface to a horizontal starting position for emergency situations. The method may further include securing the patient to the patient positioning surface. Additionally, the method may include locking the patient positioning surface during the medical procedure. Also, the method may include manually moving the patient positioning surface in at least one of the lateral and longitudinal directions.

Certain embodiments of the present invention include a patient positioning system. The patient positioning system includes a table for positioning a patient, a base attaching the table to a floor, and a user interface for controlling movement of the table. The table is capable of rotation, lift, and longitudinal motions. The table is also capable of longitudinal tilt. A region of interest of the patient is maintained in an image area during tilt.

Figure 1:
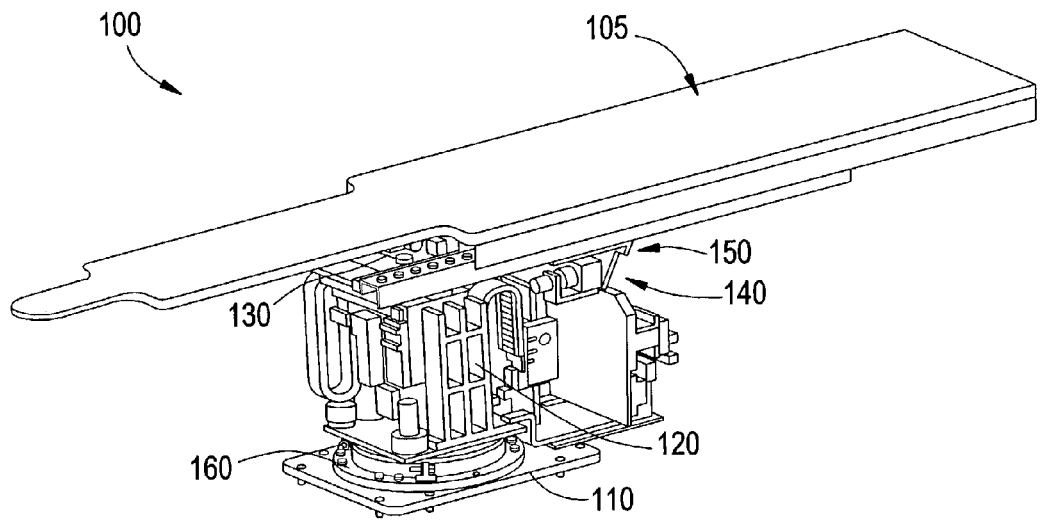
FIG. 1 illustrates a patient positioning system that is used in accordance with an embodiment of the present invention.
Figure 1:
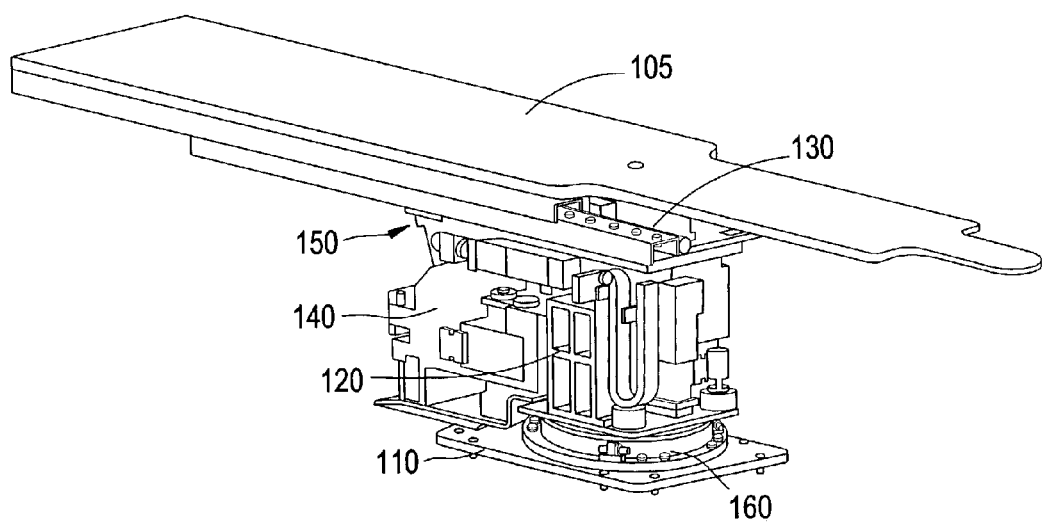

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION

FIG. 1 illustrates a patient positioning system 100 that is used in accordance with an embodiment of the present invention. The patient positioning system 100 includes a patient positioning surface 105, a base 10, a telescopic lift system 120, a longitudinal system 130, a tilt system 140, a lateral system 150 and a rotation system 160. The patient positioning system 100 is grouted, or fixed to the floor at the table base 110.

To enhance loading and unloading of a patient, the patient positioning surface 105 may rotate around a vertical axis using the rotation system 160. The patient positioning surface 105 may also be manually rotated about the rotation system 160. To move the patient to an image area, the patient positioning surface 105 may move vertically using the telescopic lift system 120 from a height at which the patient may be conveniently loaded to a height where imaging may occur (780 mm to 1080 mm, for example). To move a portion of the patient's body into the image area, the patient positioning surface 105 may move in a lateral direction (+/−140 mm from a normal imaging position, for example) using the lateral system 150.

Additionally, the telescopic lift system 120 may provide a stroke or lift motion for iso-center tracking. Iso-center is the point at which three axes of an x-ray imaging system gantry meet (not shown). Iso-center tracking maintains a patient region of interest at the iso-center during tilt or other movement of the patient positioning system 100. The intersection of the longitudinal and transverse axes (the iso-center) does not shift when the patient positioning surface 105 is tilted or rotated. Additional stroke for iso-center tracking is provided by the telescopic lift system 120 supported by a telescopic guide mechanism to accommodate a moment resulting from overhanging load.

For head to toe coverage of the patient, the patient positioning system 100 may use longitudinal motion from the longitudinal system 130. For bolus chasing (following a bolus or contrast agent through a patient's blood vessels), the longitudinal motion may be motorized with a variable speed motor (2 to 15 cm/sec, for example) using the longitudinal system 130 and a guide mechanism. In a certain embodiment, in addition to motorized motion, lateral and longitudinal axes include a clutch to support manual panning of the patient positioning surface 105. That is, the clutch may be released to allow the patient positioning surface 105 to be positioned manually by an operator.

For emerging vascular procedures, such as emergent situations (falling artery pressure, for example), venous access and CO2 studies, the patient positioning surface 105 may tilt head up and head down in the longitudinal direction (12 degrees up and 20 degrees down, for example). A region of interest of the patient may remain at the iso-center or the image area when the patient positioning surface 105 is tilted. In an embodiment, the region of interest remains in the iso-center or the image area using synchronized motion of the telescopic lift system 120, the longitudinal system 130 and the tilt system 140 as defined by the Inverse Kinematics Formula.

In an embodiment, mechanical and electrical interlocks and position feedback from the patient positioning system 100 help to ensure patient safety. Patient restraints may be provided to keep the patient on the patient positioning surface 105 and to help ensure patient safety. Certain embodiments of the patient positioning system 100 help to ensure a high level of patient safety through effective safety interlock systems and redundant systems for avoiding single point failures.

Figure 2:
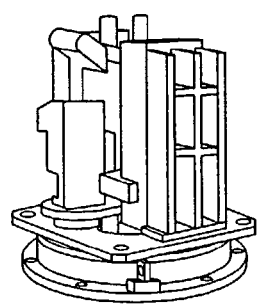
FIG. 2 illustrates a telescopic lift system used in accordance with an embodiment of the present invention.
Figure 2:
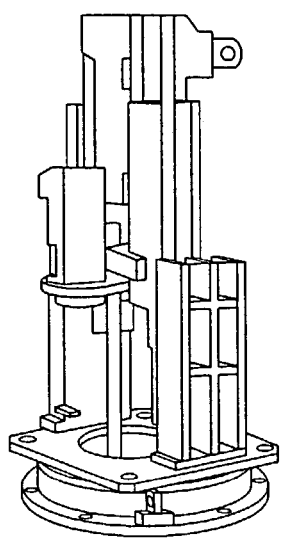
Figure 2:
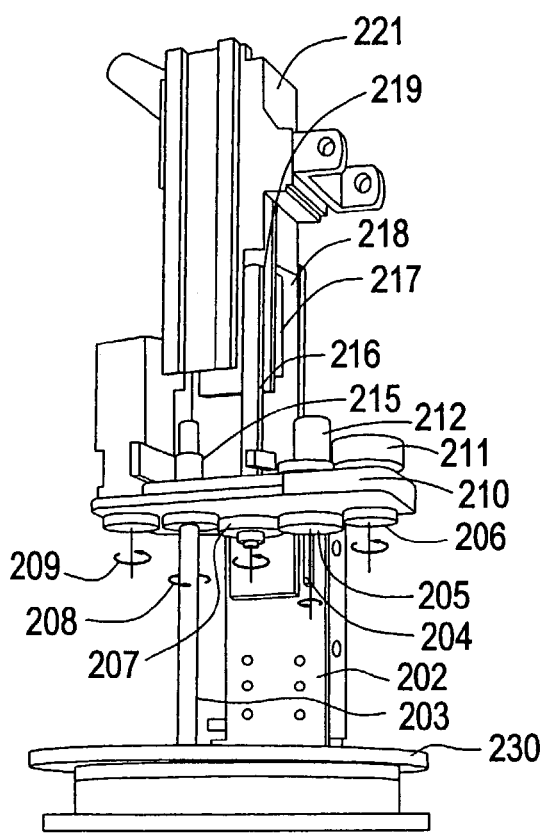
Figure 2:
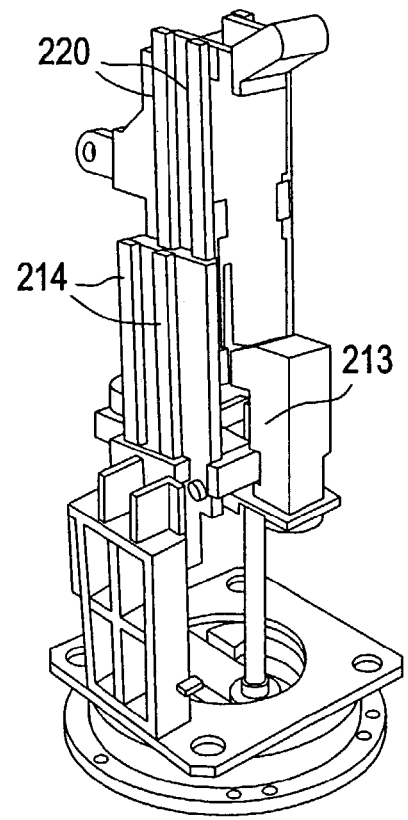

FIG. 2 illustrates a telescopic lift system 200 used in accordance with an embodiment of the present invention. The telescopic lift system 200 is similar to the telescopic lift system 120 described above in relation to FIG. 1 and the patient positioning system 100. The telescopic lift system 200 provides a stroke for lift motion to move the patient positioning surface 105 from a height where the patient may be conveniently loaded to a position where imaging occurs. In addition, the telescopic lift system 200 may also provide a stroke for vertical compensation during iso-center tracking.

The telescopic lift system 200 provides a stroke higher than that of the collapsed height of the patient positioning surface 105. In an embodiment, the telescopic lift system 200 includes a single motor 213 that drives a two-stage ball screw 203, 216. The telescopic lift system 200 has two-stage linear motion ("LM") guides (first stage LM guides 214 and second stage LM guides 220) to compensate for moments. The LM guides 214, 220 help provide accurate, consistent and smooth linear motion along the guides (rails, for example). Both stages of the telescopic lift system 200 are synchronized. Synchronizing the stages and driving both stages with a single motor 213 allows the telescopic lift system 200 to be compact, have a high load-carrying capacity, and maintain a high degree of precision. Thus, the telescopic lift system 200 addresses and improves deficiencies in stroke, load-carrying capacity, and high moment-carrying capacity that are constraints in current off-the-shelf lifting systems.

The telescopic lift system 200 includes a guidance system. The guidance system includes a main structure 202, a first stage structure 218, and a second stage structure 221. The main structure 202 of the lift system is fixed to a base 230. The main structure 202 houses first stage LM guide blocks 204 for the first stage of the telescopic lift system 200. The first stage LM guides 214 are fixed to the first stage structure 218. The first stage LM guides 214 slide through first stage LM guide blocks 204 and second stage LM guide blocks 217. In an embodiment, the first stage structure 218 has a stroke of 305 mm. The second stage structure 221 houses the second stage LM guides 220. The second stage LM guides 220 slide through the second stage LM guide blocks 217. In an embodiment, the second stage structure 221 has additional stroke (305 mm for example). In an embodiment, the combined stroke of the first stage structure 218 and the second stage structure 221 is 610 mm.

The telescopic lift system 200 also includes a drive system. Elements of the drive system are connected to the first stage structure 218 through a drive plate 210. A motor/gearbox 213 is fixed to the drive plate 210. The motor/gearbox 213 provides torque to drive stages one and two of the telescopic lift system 200. The motor/gearbox 213 includes a gear-A 209. The gear-A 209 drives a gear-B 208. The gear-B 208 is fixed to a rotary nut 215 for a stationary ball screw 203. The stationary ball screw 203 is fixed to the base 230. Rotation of the gear-A 209 and the gearB 208 translates the first stage structure 218 with the drive plate 210 through the stationary ball screw 203. The gear-B 208 also meshes a gear-C 207. The gear-C 207 rotates a second stage rotating ball screw 216. The second stage rotating ball screw 216 is housed in a bearing in the drive plate 210. The second stage rotating ball screw 216 translates a normal nut 219 in the same direction as the first stage. The normal nut 219 is fixed to the second stage structure 221. Simultaneous movement of elements of the drive system facilitates a lift stroke of, for example, 610 mm. The gear-C 207 also meshes with a gear-D 205 that is fixed to an absolute encoder 212 for motion control applications. A fail-safe electromagnetic brake 211 is located on the load side of the drive system and is fixed to a gear-E 206, which is driven by gear-D 205. The feedback from the encoder 212 sends signals to the brake 211 through a motion control system 170 (not pictured) in case of failure of any drive elements.

Figure 3:
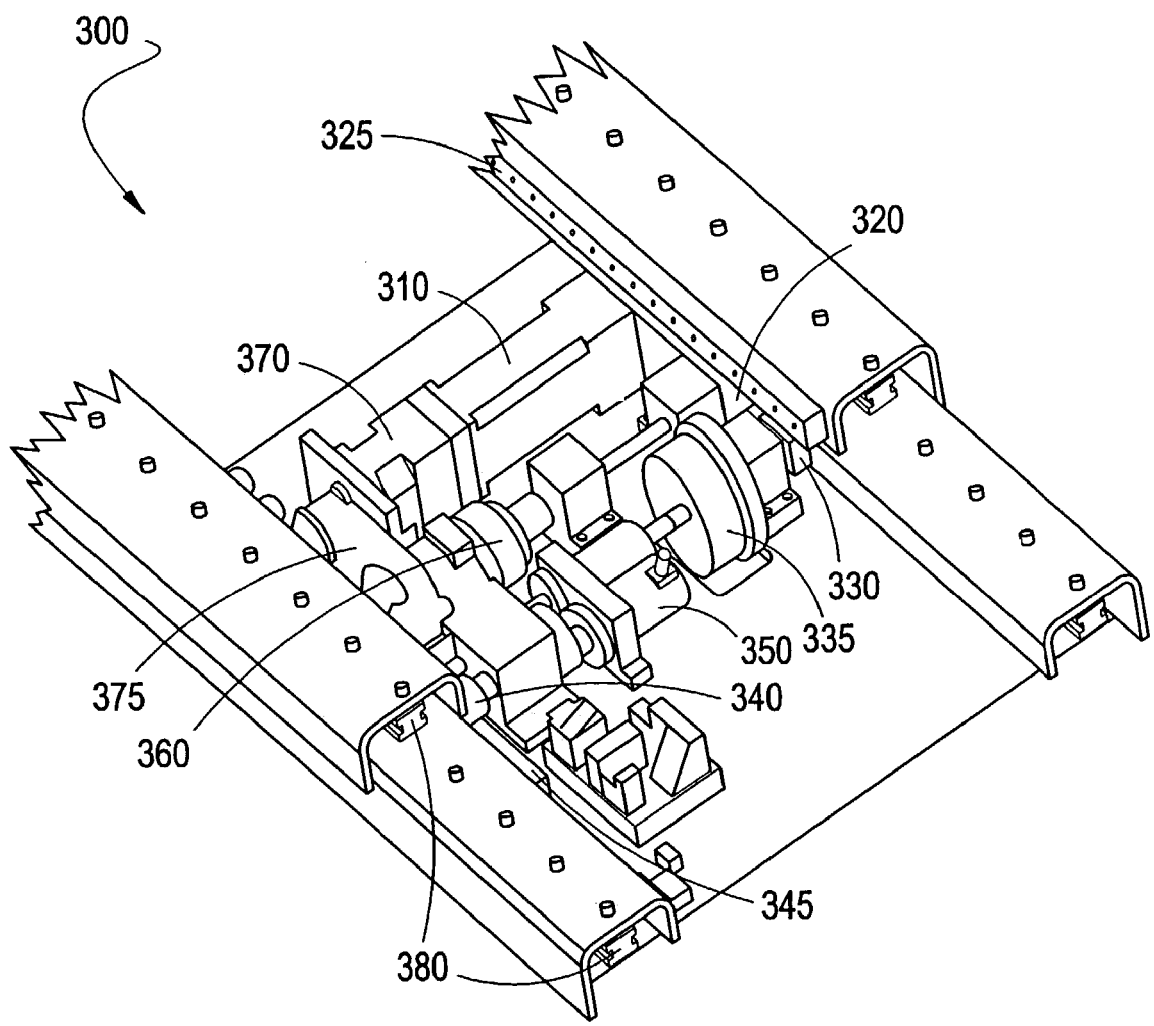
FIG. 3 illustrates a longitudinal system used in accordance with an embodiment of the present invention.

FIG. 3 illustrates a longitudinal system 300 used in accordance with an embodiment of the present invention. The longitudinal system 300 is similar to the longitudinal system 130 described above in relation to FIG. 1 and the patient positioning system 100. The patient positioning system 100 allows longitudinal motion for imaging in the forward direction (1700 mm, for example). For iso-center tracking during tilting of the patient positioning surface 105, the patient positioning surface 105 may move longitudinally in the reverse direction (25 mm, for example).

Longitudinal motion is produced by the longitudinal system 300. The longitudinal system 300 includes two-stage telescopic rails with LM guides 380. Longitudinal motion is produced through a rack and pinion mechanism driven by a motor 310. Motion of the two telescopic rails is synchronized through an additional rack and pinion mechanism. The longitudinal system 300 also includes a clutch 360 that disengages the motor 310 of the longitudinal system 300 from drive to aid in manual panning of the patient positioning surface 105. An absolute encoder 350 is used to determine the position of the patient positioning surface 105 in the longitudinal direction.

The two-stage telescopic longitudinal system 300 is divided into a top section and a bottom section. The motor 310 drives the top section. The top and bottom sections are synchronized to aid in low and uniform panning of the patient positioning surface 105 and to help avoid slippage of the bottom section during tilt of the patient positioning surface 105.

The first stage, or top c-channel, of the telescopic longitudinal system 300 is driven by a main drive pinion 320 and a main rack 325 through the motor 310. The main rack 325 drives the brake pinion 330 of the brake axis 335. The drive from the brake pinion 330 is transmitted to a synchronization pinion 340 through a drive gear and a driven gear. The drive and driven gear from a gearbox 370 determine the direction of movement of a synchronization rack 345. The synchronization pinion 340 drives the synchronization rack 345, which is mounted on to the second stage or bottom c-channel of the telescopic longitudinal system 300. The relative motion and mechanical advantage for manual panning are achieved by the gear ratio of the brake pinion 330 and synchronization pinion 340.

Figure 4:
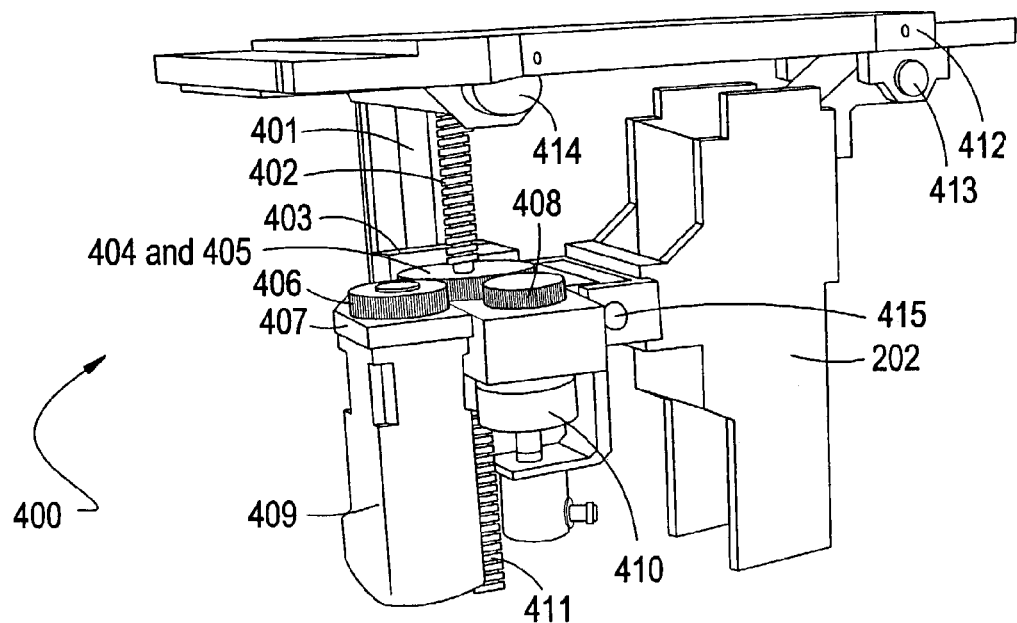
FIG. 4 depicts a tilt system used in accordance with an embodiment of the present invention.
Figure 4:
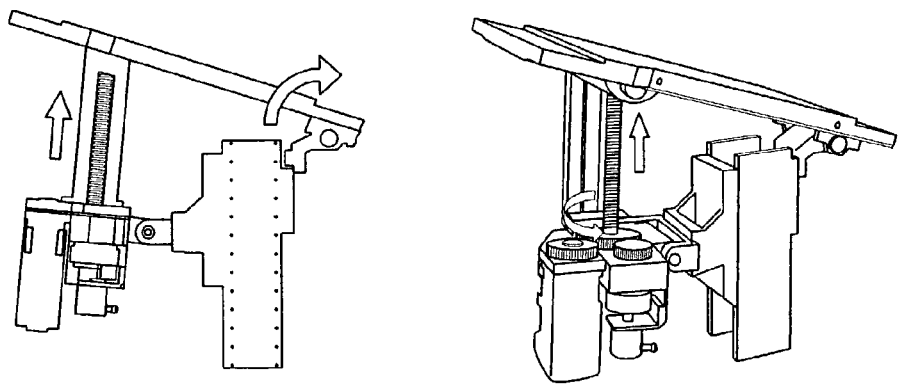
Figure 4:
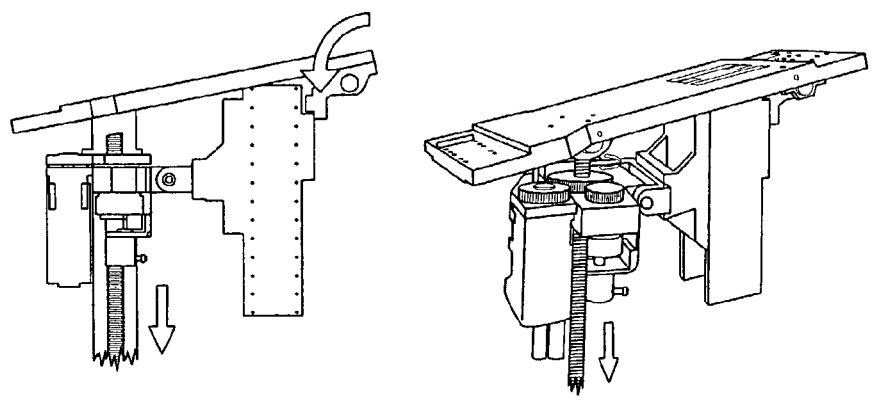

FIG. 4 illustrates a tilt system 400 used in accordance with an embodiment of the present invention. The tilt system 400 is similar to the tilt system 140 described above in relation to FIG. 1 and the patient positioning system 100. The tilt system 400 is capable of tilting the patient positioning surface 105 head up and head down in the longitudinal direction (+/−20 degrees, for example). The tilt system 400 also supports iso-center tracking during a tilt (head down at −16 degrees, for example).

The tilt system 400 includes a tilt drive system. The tilt drive system includes a ball screw 402 and a rotary nut 405 driven by a motor 409. In an embodiment, the tilt drive system is hinged at the rear side of the patient positioning surface 105. The tilt system 400 includes a LM guide 401 to compensate for moments. In an embodiment, the tilt system 400 is hinged 413 at the front side of the patient positioning surface 105. The motor 409 drives the rotary nut 405. The rotary nut 405 linearly translates the ball screw 402 for tilt about the tilt axis hinge 413 at the front of the patient positioning surface 105.

The tilt system 400 is fixed to the main structure 202 of the lift system 200. A tilt plate 412 is hinged to the main structure 202 through a tilt axis hinge 413 at the front side of the main structure 202. The tilt plate 412 is supported at the rear by an LM guide 401 and the non-rotating ball screw 402 through a hinge 414. The rotary nut 405 of the ball screw 402 and LM guide blocks 403 are housed on a plate 407 which is mounted to the main structure 202 through a hinge 415. The motor 409, as well as a brake and an incremental encoder, is mounted to the plate 407. A drive gear 406 on the motor 409 meshes with a driven gear 404 on the rotary nut 405 of the ball screw 402. The driven gear 404 also meshes with a brake gear 408. A fail-safe electromagnetic brake 410 and an absolute encoder 411 are mounted on the shaft of the brake gear 408.

The motor 409 drives the rotary nut 405 of the ball screw 402 through the drive gear 406 and the driven gear 404. The rotary nut 405 translates rotary motion into linear motion of the non-rotating ball screw 402 which may push/pull the tilt plate 412 with respect to the tilt axis hinge 413. The driven gear 404 meshes with the brake gear 408. The fail-safe electromagnetic brake 410 is mounted on to the brake gear 408 shaft. The fail-safe brake 410 may prevent the tilt system 400 from collapsing even if the drive gear 406, motor 409, and/or motor brake fails. The fail-safe electromagnetic brake 410 prevents collapse by sensing signals from the incremental encoder in the motor and the absolute encoder 411 connected to the brake gear 408 shaft through the motion control system 170.

Figure 5:
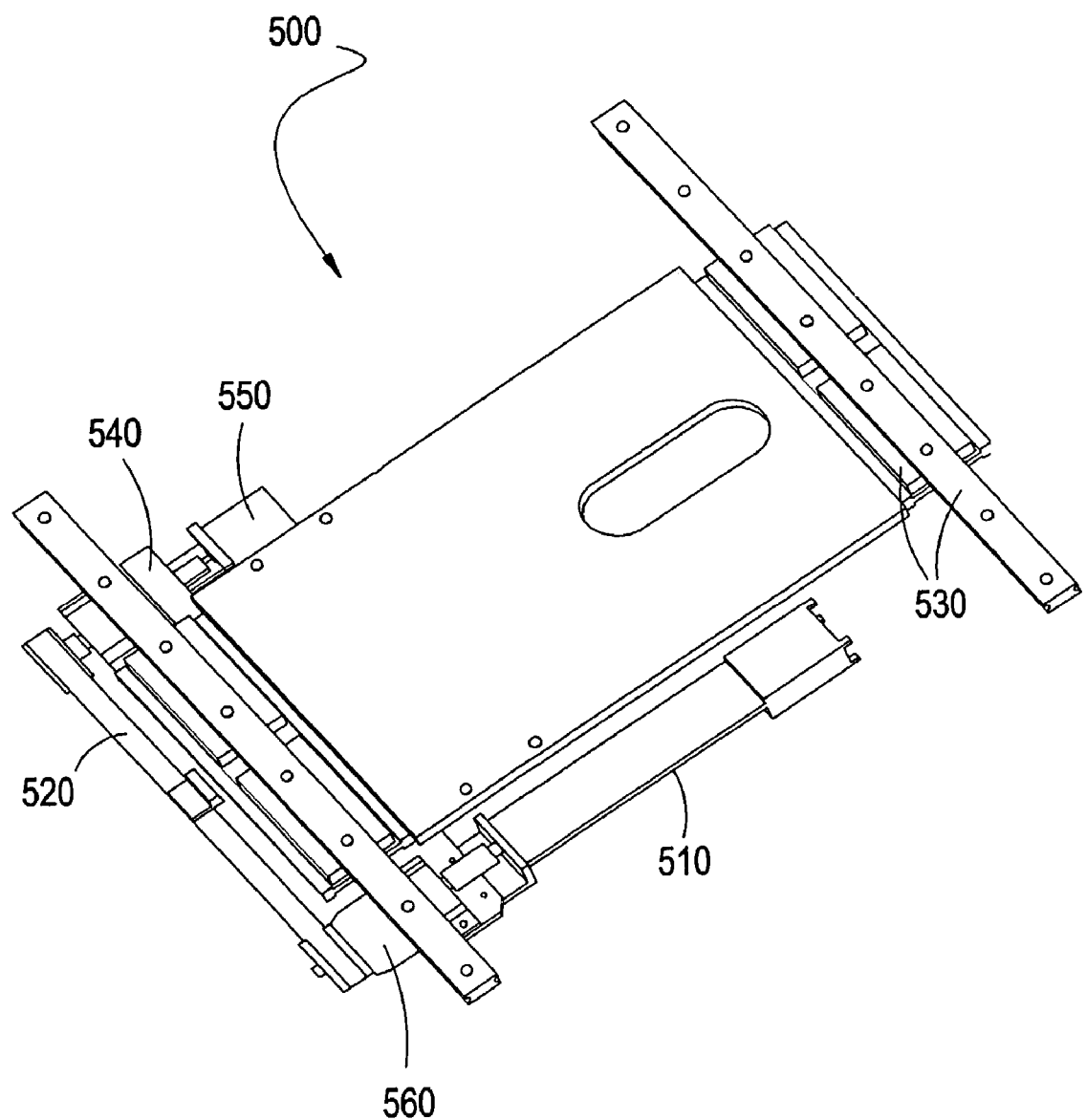
FIG. 5 depicts a lateral system used in accordance with an embodiment of the present invention.

FIG. 5 illustrates a lateral system 500 used in accordance with an embodiment of the present invention. The lateral system 500 is similar to the lateral system 150 described above in relation to FIG. 1 and the patient positioning system 100. The lateral system 500 moves the patient positioning surface 105 in the lateral direction (+/−140 mm, for example). The lateral system 500 includes a motor 510, a timing belt drive 520, LM guides 530, brake 540, and an encoder 550 for lateral movement. The lateral system 500 produces motion through the timing belt drive 520. The timing belt drive 520 is driven by the motor 510 and is guided by the LM guides 530. The lateral system 500 also includes a clutch 560 that disengages the lateral system 500 from drive by the motor 510 to aid in manual panning of the patient positioning surface 105.

The lateral system 500 and the longitudinal system 300 support both motorized and manual panning of the patient positioning surface 105. In an embodiment, a user interface (not pictured) controls the motor 310 of the longitudinal system 300 and the motor 510 of the lateral system 500 to facilitate motorized panning. For example, a joystick in the user interface may control the motors 310, 510 for motorized panning of the patient positioning surface 105. The clutches 360, 560 in the longitudinal system 300 and the lateral system 500 disengage the motors 310, 510 to facilitate manual panning.

A panning operation is carried out to move the patient to the image area in the longitudinal and/or lateral direction. Manual panning is possible when the patient positioning surface 105 is positioned horizontally. When manual panning mode is selected, the longitudinal and lateral clutches 360, 560 disengage the patient positioning surface 105 from the lateral and longitudinal motors 310, 510. Then the patient positioning surface 105 floats on the anti-friction LM guides, which allow movement of the patient positioning surface 105 in the lateral and/or longitudinal directions. The patient positioning surface 105 may be locked at any position.

Figure 6:
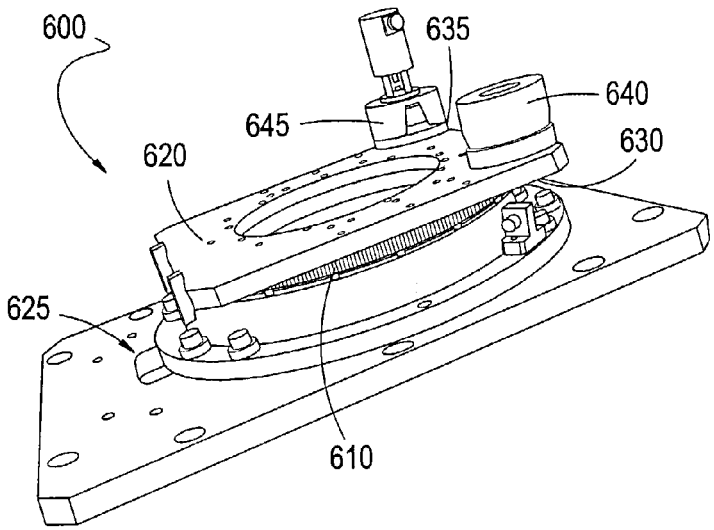
FIG. 6 depicts a rotation system used in accordance with an embodiment of the present invention.
Figure 6:
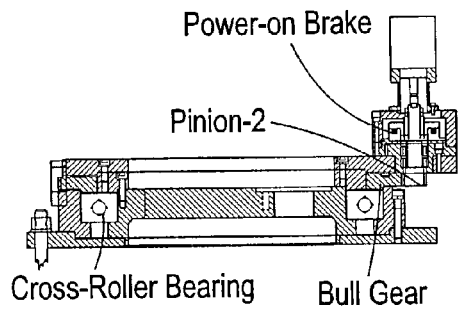
Figure 6:
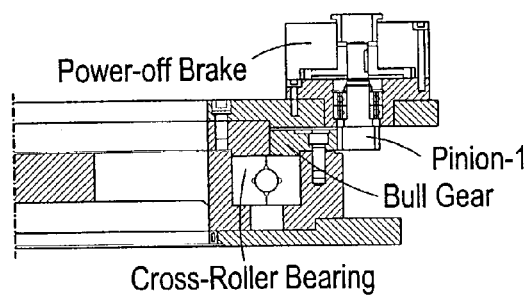
Figure 6:
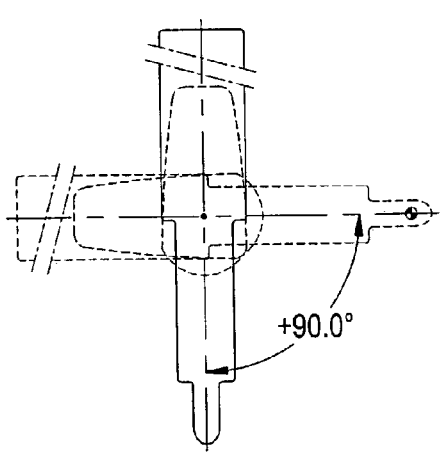
Figure 6:
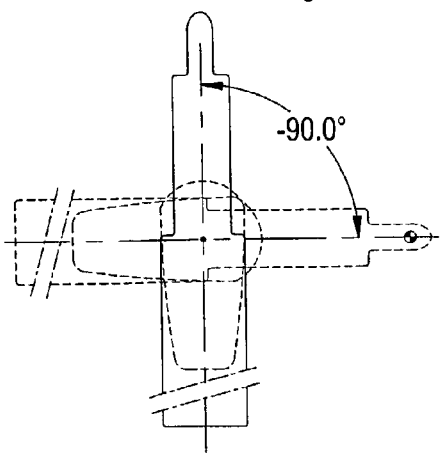

FIG. 6 illustrates a rotation system 600 used in accordance with an embodiment of the present invention. The rotation system 600 is similar to the rotation system 160 described above in relation to FIG. 1 and the patient positioning system 100. The rotation system 600 includes a bull gear 610, a bearing clamping plate 620, pinions 630, 635, a power-off brake 640, and a power-on brake 645. In an embodiment, the patient positioning surface 105 rotates manually. The rotation system 600 rotates the patient positioning surface 105 about the vertical axis (+/−90 degrees, for example). The rotation system 600 may include a docking mechanism for locating the zero position (0 degrees in the rotation axis) easily.

The bull gear 610 is machined onto the bearing clamping plate 620. The bull gear 610 is stationary. Two pinions 630, 635 are mounted at 90 degrees on the bearing housing 625. The pinions 630, 635 mesh with the bull gear 610 and rotate along with the main structure 202. The power-off brake 640 is mounted directly on the pinion 630 and the power-on brake 645 is mounted on the pinion 635. When the brake 640, 645 is applied the pinion 630, 635 holds the main structure 202 against the stationary bull gear 610. The use of a gear drive with the rotation system 600 allows torque multiplication.

In an embodiment, the patient positioning system 100 includes power-on brakes that are active when power is supplied and power-off brakes that are active when power is shut off. The rotation system 600 has a power-on brake 645 and a power-off brake 640. During medical procedures, the rotation system 600 activates both power-on and power-off brakes 640, 645 to help ensure stability and rigidity of the patient positioning surface 105. When power is off, only the power-off brake 640 may be activated for ease in removing the patient from the patient positioning surface 105.

In an embodiment, the combination of the power-on and power-off brakes 640, 645 results in three states. In the first state, power is supplied to the power-on brake 645, and no power is supplied to the power-off brake 640 (100% capacity). Both brakes 640, 645 hold the table through pinions 630, 635 and provide a rigid connection. During procedures (i.e., during imaging and while loading the patient on to the patient positioning surface 105), power is supplied only to the power-on brake 645, and both brakes 640, 645 hold the patient positioning surface 105.

In the second state, no power is supplied to both the power-on brake 645 and the power-off brake 640 (50% capacity). In a power fail condition, the power-off (failsafe) brake 640 engages, but the power-on brake 645 is released. Thus, the patient positioning surface 105 may be rotated with less effort to, for example, unload a patient in case of emergency.

In the third state, power is supplied to the power-off brake 640 and not to the power-on brake 645 (0% capacity). Thus, both brakes 640, 645 are released, and the patient positioning surface 105 is free to rotate. The free patient positioning surface 105 may be used for repeating the scans at an angle. The free patient positioning surface 105 may also be used after loading the patient to bring the patient positioning surface 105 to the zero position.

The motion control system 170 (not shown) for the patient positioning system 100 includes three major parts: a user interface, an I/O board, and servo nodes (not shown). A user may move the patient positioning surface 105 using the user interface. User interface commands are processed by the I/O board (CPU). Commands are then sent to corresponding servo nodes that control the respective axis movements. In an embodiment, a power PC-based micro controller is used as the CPU. An application program, which is running on a real-time operating system, may control the patient positioning system 100.

The patient positioning surface 105 may be prevented from tilting at the lowest position of the patient positioning surface 105, since the lowest position of the patient positioning surface 105 is used for easy loading and unloading of the patient. Each axis is provided with a power-off brake to lock the motion during a power failure and/or any malfunction of the motors and servo drives. Each axis is provided with a software limit, a hardware limit, and mechanical hard stops. An example of a software limit is the following: during normal operations, the patient positioning surface 105 shall not move beyond a certain point. An example of a hard limit is the following: the patient positioning surface 105 is controlled by a limit switch. The limit switch stops the motion of the patient positioning surface 105 if a software malfunction occurs. An example of a mechanical hard stop is as follows: an end stop is provided as backup if both software and hardware limits fail. The coordinates of all axes may be continuously monitored to avoid a collision with the ground and/or predetermined objects.

Figure 7:
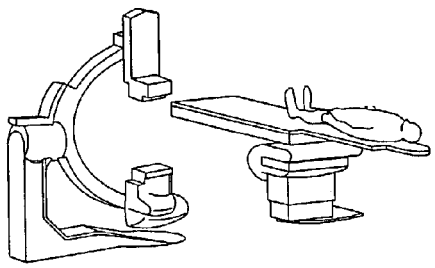
FIG. 7 depicts positions of the patient positioning surface used in accordance with an embodiment of the present invention.
Figure 7:
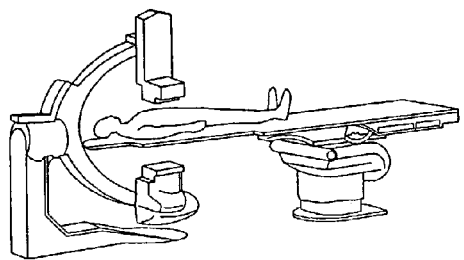
Figure 7:
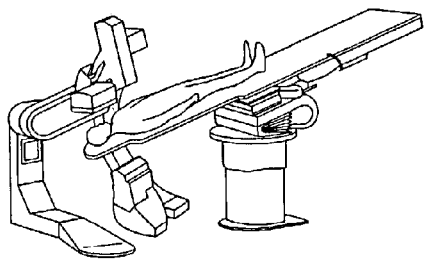
Figure 7:
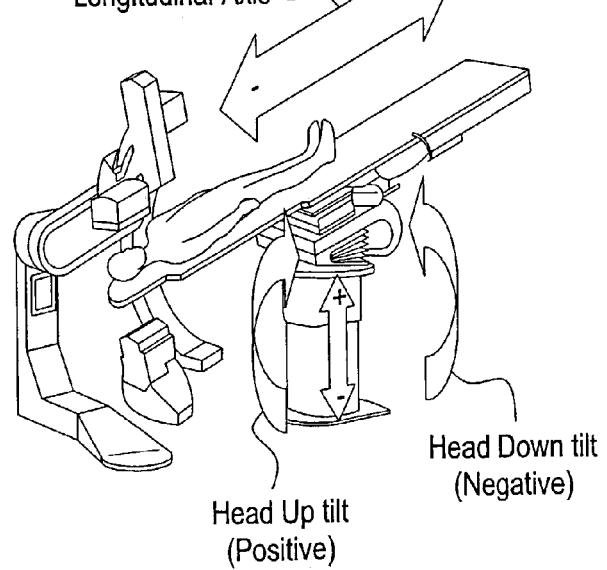
Figure 8:
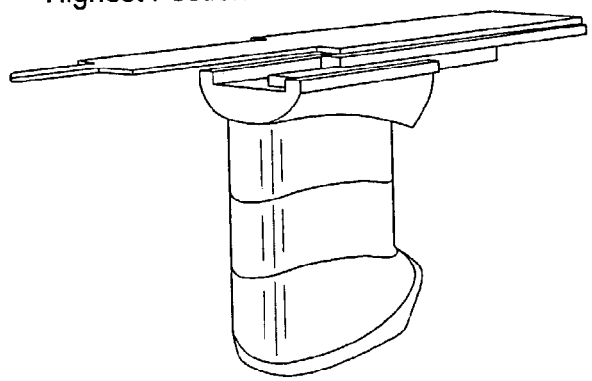
FIG. 8 shows positions of the patient positioning surface used in accordance with an embodiment of the present invention.
Figure 8:
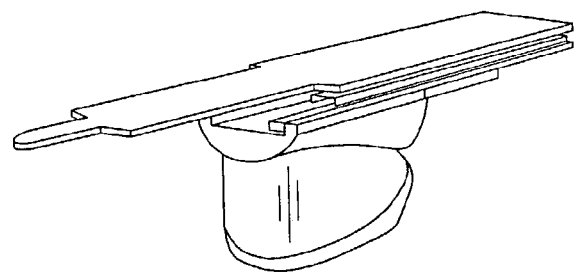
Figure 8:
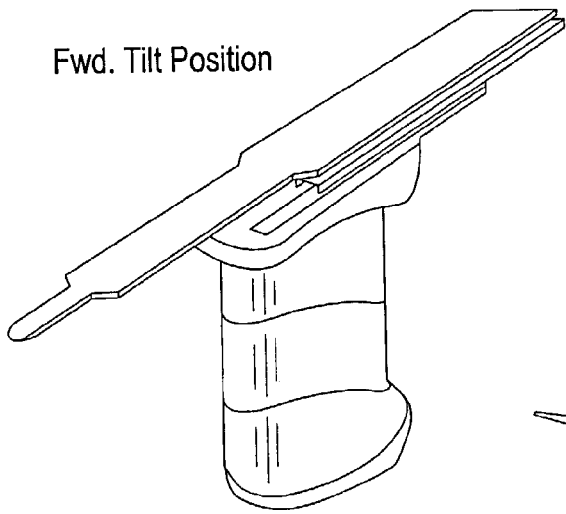
Figure 8:
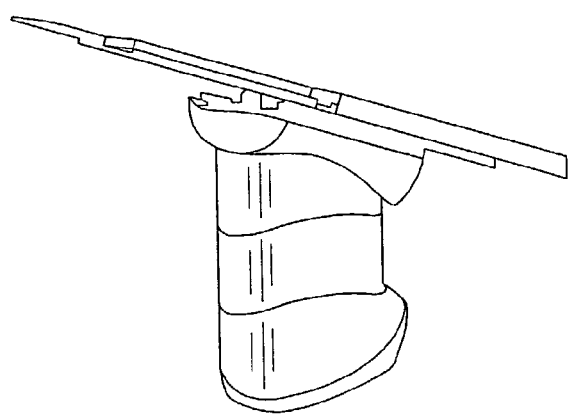
Figure 9:
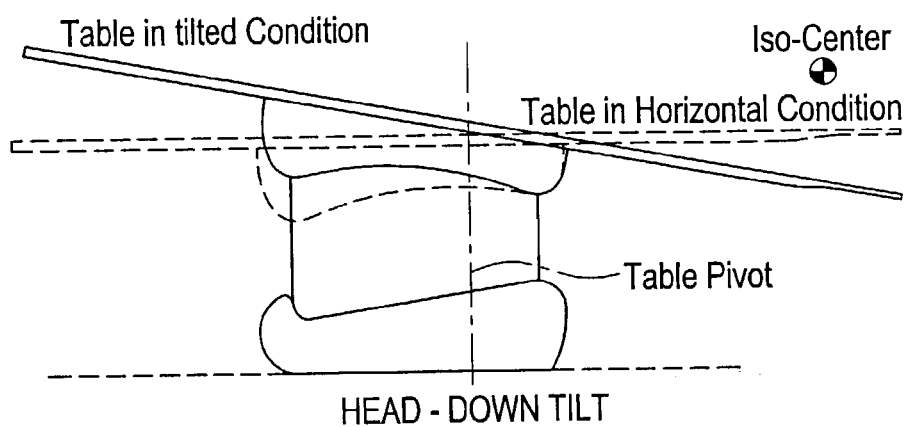
FIG. 9 depicts a tilting of the patient positioning surface with and without iso-center tracking used in accordance with an embodiment of the present invention.
Figure 9:
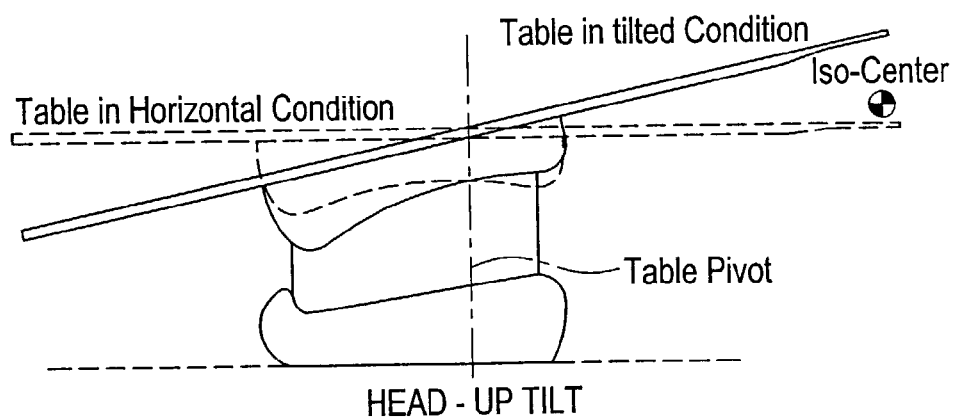
Figure 9:
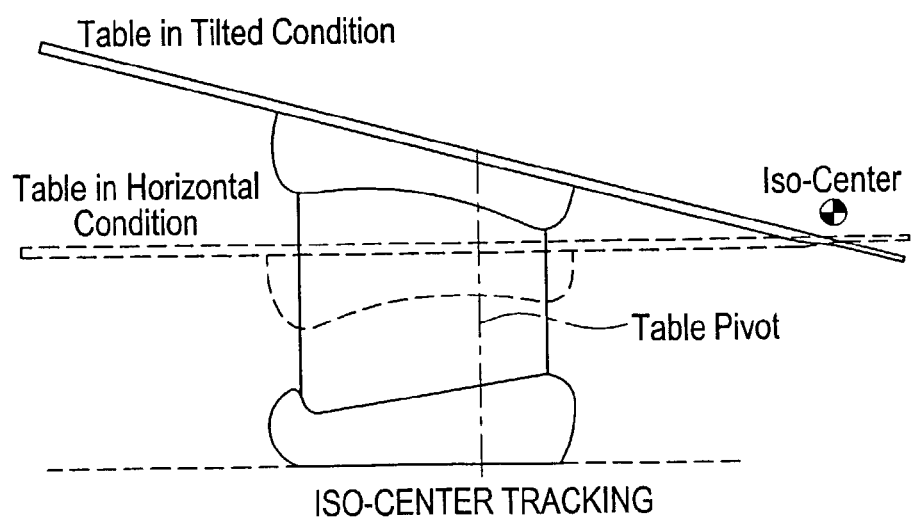

In operation, the patient positioning system 100 may tilt the patient positioning surface 105 head down or head up and/or rotate the patient positioning surface 105. FIGS. 7 and 8 illustrate some exemplary positions of the patient positioning surface 105 in an imaging system. For iso-center tracking, the telescopic lift system 200, tilt system 400, and longitudinal system 300 are simultaneously activated in an inverse kinematic relationship to keep the patient region of interest at the iso-center or image area during tilt of the patient positioning surface 105. FIG. 9 depicts a tilting of the patient positioning surface with and without iso-center tracking used in accordance with an embodiment of the present invention.

Kinematics defines relationships between positions, velocities, and accelerations of axes of motion (transverse, longitudinal, etc.) in the patient positioning system 100. Direct kinematics involves determining the position of the patient positioning surface 105 in the patient positioning system 100 in terms of angles and displacements between the axes. Inverse kinematics involves determining relationships between the axes (and the telescopic lift system 200, longitudinal system 300, and tilt system 400) based on the location of the patient positioning surface 105 and/or the patient in the patient positioning system 100.

Safety interlocks and redundant safety systems are provided to help ensure patient safety in the patient positioning system 100. In an embodiment, all axes in the patient positioning system 100 are designed to have position encoders to read the coordinates of the patient positioning surface 105 at any position at any time. Ground clearance of the patient positioning surface 105 is calculated, and motion of the patient positioning surface 105 stops if the ground clearance is less than or equal to a specified safe limit. Thus, collisions may be avoided.

In a certain embodiment, all axes are designed with redundant safety systems to avoid single point failures and to help ensure patient safety. Each motorized axis of the patient positioning system 100 may include an incremental encoder and brake (on the drive or motor side). Each motorized axis may also include an absolute encoder and brake at the load side. During normal operation, the brake at the drive side operates to stop any axis of motion. If a problem arises in the driveline, a difference in incremental encoder (drive side) and absolute encoder (load side) readings operates the brake at the load side to stop the axis. Additionally, as described above, both power-on and power-off brakes may be activated during procedures to ensure stability and rigidity of the patient positioning surface 105. During power-off conditions, only the power-off brake is activated to allow easy removal of the patient by rotating the patient positioning surface 105.

The following are some examples of operations involving the patient positioning system 100. The examples are provided to illustrate the use of components and systems in the patient positioning system 100 and are not intended to be a comprehensive list.

For example, a patient may be loaded on the patient positioning surface 105. First, the patient positioning surface 105 is positioned at 780 mm from the ground using the telescopic lift system 200. Then, the patient positioning surface 105 is rotated to the right-hand or left-hand side using the rotation system 600. Next, the patient is loaded onto the patient positioning surface 105. Patient restraints may be used to secure the patient on the patient positioning surface 105. To unload the patient, the patient positioning surface 105 is rotated to the right-hand or left-hand side using the rotation system 600. The patient positioning surface 105 is repositioned to a height of 780 mm from ground level by the lift system 200. The patient restraints are unlocked, and the patient is removed from the patient positioning surface 105.

Also, for example, the patient may be moved into the image area. First, the rotation system 600 rotates the patient positioning surface 105 to zero degrees. Next, the patient positioning surface 105 is moved vertically to the image area using the telescopic lift system 200. Then, the patient positioning surface 105 is adjusted laterally in the image area with the lateral system 500. The patient positioning surface 105 may also be adjusted longitudinally by the longitudinal system 300 to reach a desired position in the image area.

A patient may be positioned on the patient positioning surface 105 for several medical procedures and examinations. For example, in angiography, a patient's height may be adjusted by raising and lowering the patient positioning surface 105 using the telescopic lift system 200. Additionally, four-way panning may be accomplished using the lateral system 500 and the longitudinal system 300. For peripheral angiography, the patient positioning surface 105 may also be rotated into proper position using the rotation system 500 and tilted using the tilt system 400.

For bolus chasing, patient restraints may be used to secure the patient on the patient positioning surface 105. The longitudinal system 300 advances the patient positioning surface 105 in the longitudinal direction in bolus mode (015 cm/sec). For venous access and $CO_2$ studies, for example, patient restraints may keep the patient in touch with the patient positioning surface 105, and the lift 200, longitudinal 300, and tilt 400 systems may be used for iso-center tracking to maintain a desired image area during movement. In emergent situations, restraints secure the patient on the patient positioning surface 105, and the tilt system 400 tilts the patient to a desired position.

Cardiac pulmonary resuscitation (CPR) is a procedure performed for patients who suffer from cardiac arrest, for example. In order to bring a patient to a CPR position if the patient positioning surface 105 is in a horizontal position, the patient positioning surface 105 is moved longitudinally in a backward direction using the longitudinal system 300. Then, the patient positioning surface 105 is lowered using the lift system 200. If the patient positioning surface 105 is titled, the tilt system 400 returns the patient positioning surface 105 to a horizontal position. Then, the longitudinal system 300 moves the patient positioning surface 105 backward, and the lift system 200 lowers the patient positioning surface 105 to enable CPR to be performed on the patient.

Figure 10:
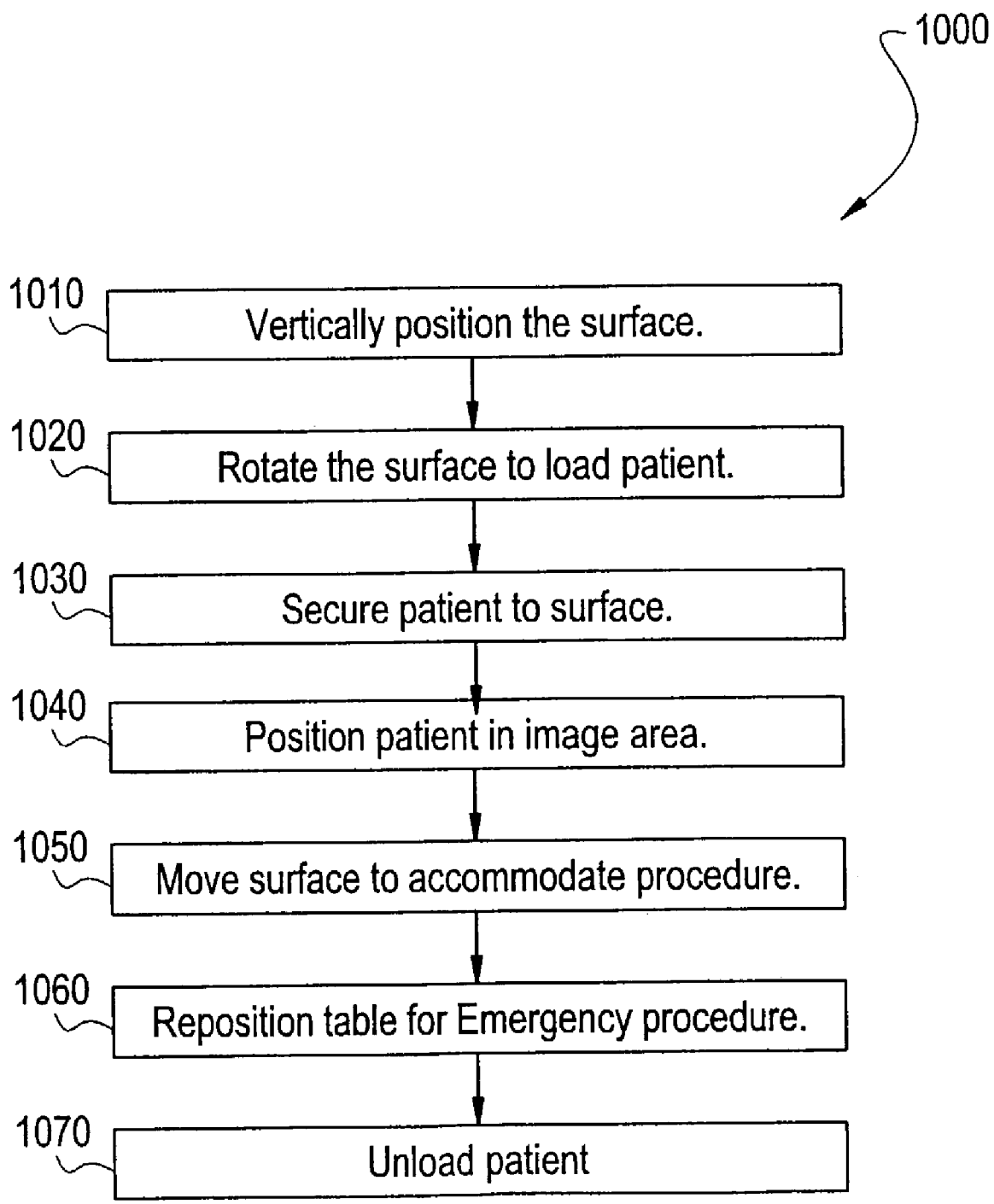
FIG. 10 illustrates a flow diagram for a method for positioning a patient in a medical imaging system used in accordance with an embodiment of the present invention.

FIG. 10 illustrates a flow diagram 1000 for a method for positioning a patient in a medical imaging system used in accordance with an embodiment of the present invention. First, at step 1010, the patient positioning surface 105 is positioned vertically at a desired distance from the ground, such as 780 mm. Then, at step 1020, the patient positioning surface 105 is rotated to allow the patient to be loaded on the patient positioning surface 105. Then, at step 1030, the patient may be secured on the patient positioning surface 105.

At step 1040, the patient is positioned in the image area. The patient positioning surface 105 is rotated, moved vertically, moved laterally, and/or moved longitudinally to position the patient or a region of interest in the patient in the image area. At step 1050, during imaging or other medical examination or procedure, the patient positioning surface 105 may be moved laterally or longitudinally, lifted, rotated, and/or tilted to accommodate the procedure. Iso-center tracking may be used to maintain the position of a patient region of interest inside the image area.

Then, at step 1060, in the event of difficulties requiring CPR or other emergency procedure, the patient positioning surface 105 may be repositioned to a horizontal position.

The patient positioning surface 105 may also be moved backward and lowered to a starting position for easy access to the patient.

Finally, at step 1070, the patient may be unloaded from the patient positioning surface 105. The patient positioning surface 105 may be rotated to allow access to the patient. The patient positioning surface 105 is adjusted to a height that will allow the patient to easily be removed. After patient restraints are removed, the patient is removed from the patient positioning surface 105.

Thus, certain embodiments of the present invention provide a fixed table that may be used for vascular and other applications. The patient positioning system 100 may rotate the patient positioning surface 105 about the vertical axis for loading and unloading patients. The rotation system 600 is equipped to adjust holding torque under power-off and power-on conditions.

The telescopic lift system 200 is used by the patient positioning system 100 to accommodate high load, moments, and lift motion or stroke to position a patient in the image area. The tilt system 300 allows the patient positioning system 100 to tilt head up or head down and maintain a desired image through iso-center tracking. The patient positioning system 100 includes a lateral system 500 to move the patient positioning surface 105 laterally using motorized and/or manual panning.

The patient positioning system supports motorized bolus chasing with head to toe coverage so that an image may be traced as the contrast agent travels through the patient. The patient positioning system 100 tracks the coordinates of the patient positioning surface 105. Positioning tracking facilitates collision avoidance with the ground and/or other predetermined objects. Tracking also allows the patient positioning system 100 to return the patient positioning surface 105 to a previously recorded and/or memorized position.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A patient positioning system for medical applications, said system comprising:
    a patient positioning surface for supporting a patient;
    a lift subsystem for adjusting elevation of said patient positioning surface;
    a longitudinal subsystem including a rack and pinion mechanical for moving said patient positioning surface in a longitudinal direction;
    a lateral subsystem for moving said patient positioning surface in a lateral direction;
    a tilt subsystem including a ball screw and rotary nut for tilting said patient positioning surface;
    a rotation subsystem for rotating said patient positioning surface; and
    a control subsystem for controlling operation of said patient positioning system, said control subsystem capable of performing iso-center tracking to maintain a region of interest of said patient in an image area during tilt by simultaneously activating said lift subsystem, said tilt subsystem and said longitudinal subsystem.

2. The system of claim 1, wherein said longitudinal subsystem and said lateral subsystem allow manual movement of said patient positioning surface in at least one of a lateral direction and a longitudinal direction.

3. The system of claim 1, further comprising a base for securing said patient positioning system, said base affixed to a floor.

4. The system of claim 1, further comprising patient restraints for securing said patient to said patient positioning surface.

5. The system of claim 1, further comprising at least one encoder for determining the position of said patient positioning surface.

6. The system of claim 5, wherein said at least one encoder allows said patient positioning surface to return to a recorded position.

7. A patient positioning system for medical applications, said system comprising:
    a patient positioning surface for supporting a patient;
    a lift subsystem for adjusting elevation of said patient positioning surface;
    a longitudinal subsystem for moving said patient position surface in a longitudinal direction;
    a lateral subsystem for moving said patient positioning surface in a lateral direction;
    a tilt subsystem including a ball screw and rotary nut for tilting said patient positioning surface, one or more encoders, and an electromagnetic brake, said brake configured to prevent said tilt subsystem from collapsing by sensing signals from said encoders;
    a rotation subsystem for rotating said patient positioning surface; and
    a control subsystem for controlling operation of said patient positioning system,
    wherein said lift subsystem adjusts elevation of said patient positioning surface using a two-stage synchronized telescopic lift system.

8. A patient positioning system for medical applications, said system comprising:
    a patient positioning surface for supporting a patient;
    a lift subsystem for adjusting elevation of said patient positioning surface;
    a longitudinal subsystem for moving said patient positioning surface in a longitudinal direction;
    a lateral subsystem for moving said patient positioning surface in a lateral direction;
    a tilt subsystem including a ball screw and rotary nut for tilting said patient positioning surface, one or more encoders, and an electromaenetlc brake, said brake configured to prevent said tilt subsystem from collapsing by sensing signals from said encoders;
    a rotation subsystem for rotating said patient positioning surface; and
    a control subsystem for controlling operation of said patient positioning system,
    wherein said longitudinal subsystem moves said patient positoning surface in a longitudinal direction using a two-stage synchronized telescopic longitudinal system.

9. A patient positioning system for medical applications, said system comprising:
    a patient positioning surface for supporting a patient;
    a lift subsystem for adjusting elevation of said patient positioning surface;
    a longitudinal subsystem for moving said patient positioning surface in a longitudinal direction;
    a lateral subsystem for moving said patient positioning surface in a lateral direction;

a tilt subsystem for tilting said patient positioning surface;
a rotation subsystem for rotating said patient positioning surface
a control subsystem for controlling operation of said patient positioning system;
a power-on brake for braking when a voltage is supplied to said power-on brake; and
a power-off brake for braking when a voltage is removed from said power-off brake.

10. The patient positioning system of claim 9, wherein said longitudinal subsystem includes a rack and pinion mechanism.

11. The system of claim 9, wherein said longitudinal subsystem moves said patient positioning surface in a longitudinal direction using a two-stage synchronized telescopic longitudinal system.

12. The system of claim 9, wherein said tilt subsystem includes a ball screw and rotary nut.

13. The system of claim 9, wherein said lift subsystem adjusts elevation of said patient positioning surface using a two-stage synchronized telescopic lift system.

14. The system of claim 9, further comprising a base for securing said patient positioning system, said base affixed to a floor.

15. The system of claim 9, further comprising patient restraints for securing said patient to said patient positioning surface.

16. A method for positioning a patient for medical applications, said method comprising:
vertically positioning a patient positioning surface to a desired height to allow a patient to be loaded onto the patient positioning surface;
rotating the patient positioning surface to a position to allow a patient to be loaded onto the patient positioning surface;
loading a patient on the patient positioning surface;
positioning the patient for a medical procedure, said positioning step comprising at least one of rotating, lifting, lateral motion, longitudinal motion, and longitudinal tilting of the patient positioning surface;
maintaining a region of interest of the patient by tilting the patient positioning surface during a procedure involving movement of the patient positing surface,
preventing said patient positioning surface from collapsing by sensing signals from one or more encoders; and
returning the patient positioning surface to a horizontal starting position for emergency situations.

17. The method of claim 16, further comprising securing the patient to the patient positioning surface.

18. The method of claim 16, further comprising locking the patient positioning surface during the medical procedure.

19. The method of claim 16, further comprising manually moving the patient positioning surface in at least one of the lateral and longitudinal directions.

20. A method for positioning a patient for medical applications, said method comprising:
vertically positioning a patient positioning surface to a desired height to allow a patient to be loaded onto the patient positioning surface;
rotating the patient positioning surface to a position to allow a patient to be loaded onto the patient positioning surface;
loading a patient on the patient positioning surface;
positioning the patient for a medical procedure, said positioning step comprising at least one of rotating, lifting, lateral motion, longitudinal motion and longitudinal tilting of the patient positioning surface;
maintaining a region of interest of the patient by
simultaneously activating a lift subsystem, a tilt subsystem, and a longitudinal subsystem; and
unloading the patient from the patient positioning surface.

21. A grouted tilting patient positoning system for vascular applications, said system comprising:
a base for securing said patient positioning system, said base affixed to a floor;
a patient positioning surface for supporting a patient;
a telescopic lift subsystem for adjusting elevation of said patient positioning surface;
a telescopic longitudinal subsystem including a rack and pinion mechanism for moving said patient positioning surface in a longitudinal direction;
a lateral subsystem for moving said patient positioning surface in a lateral direction;
a tilt subsystem including a ball screw and rotary nut for tilting said patient positioning surface; and
a rotation subsystem for rotating said patient positioning surface,
wherein said tilt subsystem, said tilt subsystem, and said longitudinal subsystem are capable of being simultaneously activated to keep a region of interest in an image area during tilt.

22. The system of claim 21, further comprising patient restraints for securing said patient to said patient positioning surface.

23. The system of claim 21, further comprising at least one encoder for determining the position of said patient positioning surface.

24. The system of claim 23, wherein said at least one encoder allows said patient positioning surface to return to a recorded position.

25. The system of claim 21, further comprising a control subsystem for controlling operation of said patient positioning system.

26. The system of claim 25, wherein said control subsystem performs iso-center tracking to maintain a region of interest of said patient in an image area during tilt.

27. The system of claim 25, wherein said control subsystem avoids collision with at least one of the ground and a predetermined object by continuously monitoring coordinates of all axes of motion, calculating a clearance from said at least one of said ground and said predetermined object, and stopping motion of said patient positioning surface if said clearance is less than or equal to a specified safe limit.

28. A grouted tilting patient positioning system for vascular applications, said system comprising:
a base for securing said patient positioning system, said base affixed to a floor;
a patient positioning surface for supporting a patient;
a telescopic lift subsystem for adjusting elevation of said patient positioning surface;
a telescopic longitudinal subsystem for moving said patient positioning surface in a longitudinal direction;
a lateral subsystem for moving said patient positioning surface in a lateral direction;
a tilt subsystem for tilting said patient positioning surface;
a rotation subsystem far rotating said patient positioning surface
a power-on brake for braking when a voltage is supplied to said power-on brake; and a power-off brake for braking when a voltage is removed from said power-off brake.

29. The system of claim 28, further comprising a control subsystem for controlling operation of said system.

30. The system of claim 29, wherein said control subsystem performs iso-center tracking to maintain a region of interest of said patient in an image area during tilt.

31. The system of claim 29, wherein said control subsystem avoids collision with at least one of the ground and a predetermined object by continuously monitoring coordinates of all axes of motion, calculating a clearance from said at least one of said ground and said predetermined object, and stopping motion of said patient positioning surface if said clearance is less than or equal to a specified safe limit.

32. The system of claim 28, further comprising at least one encoder for determining the position of said patient positioning surface.

33. Tic system of claim 32, wherein said at least one encoder allows said patient positioning surface to return to a recorded position.

34. A patient positioning system, said system comprising:
 a table for positioning a patient, said table capable of rotation, lift and longitudinal motions, said table capable of longitudinal tilt using a ball screw and rotary nut, wherein a region of interest of said patient is maintained in an image area during tilt by tilting said table in an inverse kinematic relationship with simultaneous lifting and longitudinal movements of said table;
 a base attaching said table to a floor; and
 a user interface for controlling movement of said table.

* * * * *

UNITED STATES PATENT AND TRADEMARK OFFICE
CERTIFICATE OF CORRECTION

PATENT NO. : 6,986,179 B2
DATED : January 17, 2006
INVENTOR(S) : Varadharajulu et al.

It is certified that error appears in the above-identified patent and that said Letters Patent is hereby corrected as shown below:

Column 11,
Line 53, delete "mechanical" and insert -- mechanism --.

Column 12,
Line 22, delete "position" and insert -- positioning --.
Line 49, delete "electromaenetlc" and insert -- electromagnetic --.

Column 13,
Line 3, insert -- ; -- after "surface".

Column 14,
Line 65, insert -- ; -- after "surface".

Column 16,
Line 1, delete "Tic" and insert -- The --.

Signed and Sealed this

Second Day of May, 2006

JON W. DUDAS
*Director of the United States Patent and Trademark Office*